United States Patent [19]

Cabasso

[11] 4,112,068

[45] Sep. 5, 1978

[54] CANINE LUNG CELL STRAIN CULTURE SYSTEMS AND PROCESSES FOR THE CULTIVATION OF VIRUSES AND VACCINES THEREFROM

[75] Inventor: Victor J. Cabasso, Moraga, Calif.

[73] Assignee: Cutter Laboratories, Inc., Berkeley, Calif.

[21] Appl. No.: 828,369

[22] Filed: Aug. 29, 1977

Related U.S. Application Data

[63] Continuation-in-part of Ser. No. 713,547, Aug. 11, 1976, abandoned, which is a continuation of Ser. No. 576,527, May 12, 1975, abandoned.

[51] Int. Cl.$^2$ ............... A61K 39/12; A61K 39/28; C12K 9/00
[52] U.S. Cl. ............... 424/89; 195/1.1; 195/1.2; 195/1.3; 195/1.5; 195/1.8
[58] Field of Search ............... 195/1.1, 1.2, 1.3, 1.8; 424/89

[56] References Cited

U.S. PATENT DOCUMENTS 3,462,526   8/1969   Ratuld et al. ............ 424/90

*Primary Examiner*—Sam Rosen
*Attorney, Agent, or Firm*—Robert E. Allen; Bertram Bradley

[57] ABSTRACT

A finite cell strain is derived from canine fetal lung tissue, the cells of which are fibroblast-like, diploid, and are free of reverse transcriptase and C-type particles. With a nutrient medium the cells provide a cell culture system useful in the cultivation of a number of viruses from which vaccines may be prepared.

10 Claims, No Drawings

CANINE LUNG CELL STRAIN CULTURE SYSTEMS AND PROCESSES FOR THE CULTIVATION OF VIRUSES AND VACCINES THEREFROM

This is a continuation-in-part of application Ser. No. 713,547, filed Aug. 11, 1976, which application is a continuation of application Ser. No. 576,527, filed May 12, 1975, both now abandoned.

BACKGROUND OF THE INVENTION

This invention relates to the preparation of a new cell strain, to the cultivation of viruses therein, and to the production of vaccines from said viruses.

There are a number of problems associated with the growing of viruses for the production of vaccines. Viruses are grown on cell cultures and a suitable cell culture must be found for each specific virus from which a vaccine is to be made. A specific virus is generally found to grow or may be adapted to grow in only one or a few cell cultures. To be economically feasible in commercial vaccine production, the rate of growth of a virus in a particular cell culture must be reasonably rapid. In addition, the rate of growth of the cells in a cell culture must also be sufficiently rapid in order to provide reasonable quantities of cells on which the virus can grow.

Cell cultures generally used for virus cultivation are either primary cell cultures or they are cell strains or cell lines. Primary cell cultures are started from cells, tissues or organs taken directly from an organism and is regarded as a primary cell culture until it is subcultured for the first time. A cell line or cell strain arises from a primary culture at the time of the first subculture. They are either "finite" or "continuous", i.e., they are "finite" if the cells will grow for a limited number of passages before senescence occurs or they are "continuous" if they appear to be capable of growing for an infinite number of passages.

Primary cultures are generally undesirable in commercial vaccine production since fresh tissue must be obtained from new donors for every lot of vaccine produced, with the attendant risk of viral, bacterial and fungal contamination with each new batch of tissue.

Although there are several continuous cell lines available for veterinary vaccine manufacture, such cell cultures are not considered acceptable in the production of vaccines for human use. The reason for this is that when a cell line becomes continuous, the cells are no longer diploid but have become heteroploid. It is generally believed that such heteroploid cells may carry a greater potential for oncogenicity. The most desirable cells for cultivation of viruses to be used in vaccine production, particularly for human use, are therefore those from finite cells strains or lines which remain diploid and have good growth rates which are substantially uniform over a large number of passages. Oftentimes, attempts to obtain such strains result in those which show senescence after only a few passages or the cells may become heteroploid even though the strain is a finite strain.

At the present time, vaccines for the treatment or prevention of rabies have several shortcomings, particularly in the treatment of humans. One such vaccine derived from rabies virus grown on duck embryos is of low antigenicity and thus requires a prolonged and painful course of treatment. Another cell culture for rabies virus cultivation which is suitable for a vaccine for human use is a finite diploid cell strain derived from human fetal lung tissue. There are some who feel diploid cell strains other than those derived from human tissues would be more desirable for virus cultivation intended for human vaccines since the possibility for other cell strains to harbor a latent or undetectable virus to which humans might be susceptible would be more remote.

A fibroblastic cell culture derived from fetal dog lung tissue was described by de Ratuld and Werner (Ann Inst. Pasteur 112, 802, 1967) which they sub-cultured for between 10 and 30 passages in order to determine whether this particular organ (lung) in the dog fetus carried a Herpes-like virus. These same authors in U.S. Pat. No. 3,462,526 described the use of a fibroblastic cellular strain from fetal dog lung for the cultivation of this same virus.

SUMMARY OF THE INVENTION

A finite cell strain has been produced whose cells have been found to be suitable as a growth medium for the cultivation of a number of viruses either for research purposes or for commercial production of vaccines. The cell strain (designated CLDLu) is derived from fetal canine lung tissue from which the first cell culture has been successfully subcultured with substantially uniform growth rates over a large number of passages. The cells of this cell strain are fibroblast-like and by chromosome analysis have been shown to be entirely canine and to remain diploid throughout their passage range. They have also been demonstrated to be non-oncogenic and non-tumorigenic, to be free of adventitious viruses, and do not harbor latent viruses as determined by tests conducted in accord with Standard Requirement P-72 published by the Veterinary Biologics Division of the USDA.

The cell strain of this invention is further characterized by its being free of reverse transcriptase and C-type particles. C-type particles are RNA viruses which contain reverse transcriptase which has been demonstrated to be oncogenic in animals. C-type particles are frequently found in all species of animals. Thus, a cell strain culture which is free of reverse transcriptase and C-type particles would be particularly desirable for cultivating viruses in the production of vaccines, especially those intended for human use, since the potential oncogenesis from reverse transcriptase is thereby avoided.

With care in the process of obtaining the cell strain, separate lots of the cell strain can be produced from lung tissue of the same or different fetuses, each having similar characteristics or properties as indicated above. One such lot of the cell strain has been deposited with the American Type Culture Collection, Rockville, Md. 20852, as A.T.C.C. No. CL-175.

The present invention includes a cell culture system comprising cells of the CLDLu cell strain in a nutrient medium which is suitable for growth of the cells so as to provide a medium for the cultivation of a number of viruses. Preferably such a cell culture system incorporates fetal bovine serum. A preferred composition in the cell culture system comprises an inoculum of about $4 \times 10^6$ of the CLDLu cells in a solution which is about 80–90% with respect to Eagle's MEM, about 0.15% with respect to Earle's BSS with bicarbonate and between 10–20% fetal bovine serum. Other tissue culture media formulations may be used for supporting the CLDLu cells.

The cell culture system according to the present invention may be used for the cultivation of a variety of viruses including: rhabdoviruses, for example PV-12 and HEP Flury strains of rabies virus; paramyxoviruses, for example parainfluenza virus type 3 and canine distemper virus; orbiviruses, for example bluetongue virus; and herpesviruses, for example infectious bovine rhinotracheitis virus. Of particular interest is the finding that rabies virus, e.g. PV-12 and HEP Flury strains, can be adapted to grow in the cells of the CLDLu cell strain and to yield high titers of the virus suitable for vaccines for either veterinary or human use.

The production of vaccines also falls within the scope of the present invention. Viruses cultivated from the cell culture system of this invention are further processed to obtain vaccines by methods known in the art. Thus the end product of a virus cultivation may be used as such or may be attenuated or inactivated by any known procedures to give non-disease producing antigenic material which may be incorporated into an administrable form and dosage as a vaccine for stimulating the production of antibodies by the host for active immunization. The dosage form may include such preparations which are suitable for intranasal, oral, or parenteral administration and may include physiologically acceptable adjuvants or other delayed release means as well as salts and/or buffering agents.

The invention will be better understood as illustrated in the following examples.

DETAILED DESCRIPTION

Production of the Cell Strain

Example 1

Lung tissue obtained from a female fetus aseptically removed from a bitch in about her 50th day of gestation was minced, trypsinized for 5 minutes at 37° C. using 0.25 percent trypsin solution, and allowed to grow in a 75 cm.$^2$ bottle in a medium composed of 89.85 percent Eagle's MEM in 0.15 percent Earle's BSS with sodium bicarbonate (1.43 g./L.) supplemented with 10 percent fetal bovine serum. Antibiotics (penicillin, 100 units/ml. and streptomycin, 100 mcg./ml.) and fungicide (amphotericin B, 2.5 mcg./ml.) were included. Cell population approximately doubled at 35°–37° C. between 2 and 3 days. Following trypsinization and cultivation in the same medium for two additional passages, improved cell growth was obtained by increasing the fetal bovine serum to 20 percent in the fourth to the 15th passage. In the 15th sub-cultivation, the medium was further modified by the inclusion of 0.01 M HEPES buffer. The cells obtained in the 15th sub-culture were frozen to provide a master cell seed stock (MCS) which was used in the same modified medium and sub-cultured for 20 additional passages (MCS+20). Senescence was apparent at about the 55th passage. Cells from the 15th passage (MCS) and cells from the 35th passage (MCS+20) were characterized.

Cells from MCS and MCS+20 were fibroblast-like and were free of adventitious viruses, yeast, bacteria, fungi and mycoplasma, as determined in accord with Standard Requirement P-72 of the United States Department of Agriculture (USDA) Animal & Plant Health Inspection Service, APHIS, Veterinary Services (formerly Veterinary Biologics Services (VBS)). When a more sensitive test for mycoplasma was later developed and applied as described in paragraph 610.30, subpart D, of Title 21 of the Code of Federal Regulations, mycoplasma was detected.

Results of the chromosome analysis of the cells are shown in Table I below and show the cells to be canine and the retention of the diploid karyotype.

TABLE I

| CHROMOSOME FREQUENCY DISTRIBUTION IN 50 CLDLu CELLS | | | | | | | | | | | | | | | | | |
|---|---|---|---|---|---|---|---|---|---|---|---|---|---|---|---|---|---|
| Chromosomes | 59 | 63 | 65 | 68 | 69 | 71 | 72 | 73 | 74 | 75 | 76 | 77 | 78 | 79 | 80 | 81 | 82 |
| Cells - MCS |  | 1 |  | 1 | 2 |  | 2 | 1 | 3 | 3 | 3 | 3 | 23 (46%) | 5 |  | 2 | 1 |
| Cells - MCS+20 | 1 |  | 1 |  |  | 2 |  | 3 | 2 | 2 | 8 | 3 | 22 (44%) | 3 | 2 |  | 1 |

Karyotypic analysis for the MCS and MCS+20 cells also confirmed the morphological similarity between the 20 passage range.

Tumorigenicity and oncogenicity tests were performed in cortisone stressed hamsters in accord with VBS Standard Requirement P-72, Attachment B, as published by the Veterinary Biologics Division of the USDA, July 1, 1970. There was no evidence of tumor formation and no abnormalities were detected in cheek pouches or organs in the body cavities of the hamsters.

The test for reverse transcriptase, a specific indicator of C-type particles, was performed according to the method described by Milstien, J. B. and Petricciani, J. C., J. Clin. Microbiol. 1 (No. 4), 353, 1975, and the cells were found free of it.

The test for non-canine cells by immunofluorescence technique in accord with VBS Standard Requirement P-72, Attachment D, published July 1, 1970, confirmed canine identity of the cell strain and demonstrated freedom from contamination with heterologous species of cells in concurrent use in our laboratories.

Example 2

Lung tissue obtained from 10 fetuses aseptically removed from a bitch in about her 44th day of gestation was pooled, minced and trypsinized three times for 20 minutes duration at 37° C. First growth and subsequent subculturing was accomplished in a manner similar to that described in Example 1 except that the culture medium was supplemented with only 10 percent fetal bovine serum throughout all passages. To assure the trypsin and fetal bovine serum would not contribute to any possible contamination of the cells with mycoplasma, these materials prior to their use were tested using the more sensitive assay referred to above and found to be free of mycoplasma.

Cells obtained in the tenth subculture were frozen to provide a master cell stock which was used for subculturing for eight additional passages at which point senescence became apparent.

Cells from the 11th and 16th passages were demonstrated to be fibroblast-like, diploidal, free of mycoplasma, yeast, bacteria, fungi and adventitious viral agents, and to be non-tumorigenic and non-oncogenic as well as being free of C-type particles and reverse transcriptase according to tests referred to in Example 1.

Example 3

Lung tissue from each of six fetuses removed from a bitch in her 46th day of gestation was used individually for subculturing the fibroblast-like cells therefrom. One of the individual cell strains was subcultured for about 20 passages and another individual cell strain was subcultured up to 35 passages before senescence became apparent.

General Method for the Cultivation of Viruses In the CLDLu Cell Strain

CLDLu cells were infected either in suspension or following formation of a confluent monolayer in culture vessels such as tubes or 32 oz. bottles. Appropriately diluted virus, such as 0.2 ml. of a $10^{-2.0}$ to $10^{-3.5}$ dilution of virus, representing a multiplicity of infection of 0.0001 to 1.0, was added to the culture vessels containing the cells, generally about $4 \times 10^6$ cells. If the virus was added to the suspended cells an adsorption period of about 1 hour at 34°–37° C. was required. Diluted virus which was added to cell monolayers remained in contact with the cells for a period of time such as 0.5 to 1 hour at 34°–37° C. to permit adsorption to take place. For cells infected in suspension, growth medium consisting of about 80–85 percent Eagle's MEM in about 0.15 percent Earle's balanced salt solution, supplemented with 15 to 20% fetal bovine serum provided the necessary nutrients to permit monolayer formation to take place. Exclusion of microbial contaminants was fostered by the presence of combinations of antibiotic formulations such as 100 units/ml. of penicillin and 100 mcg./ml. of streptomycin or 30 units/ml. neomycin and 30 units/ml. of polymyxin, plus 2.5 mcg./ml. of amphotericin B. The pH of the growth and maintenance medium was controlled by the addition of 0.01 M HEPES buffer and 0.19% sodium bicarbonate.

Following incubation at 34°–37° C. for a period sufficient to permit viral replication to take place, infected fluids were harvested when, in the case of cytolytic viruses, 70–90% of the infected cells exhibited a typical cytopathogenic effect. For non-cytolytic viruses, the infected fluids were harvested when the peak of viral growth had taken place as shown by previous growth curve titrations, typically 2–7 days after infection. Multiple cycles of viral harvests of infected fluids were also possible in the case of non-cytolytic viruses, by removal of spent medium, the addition of fresh medium, and continued incubation of the infected cells until a new peak of viral growth was achieved in 1–3 days.

Cultivation of Rhabdovirus in the CLDLu Cell Strain

Example 4

To adapt rhabdoviruses to the cell culture system, PV-12 or HEP Flury strains of rabies virus were grown in CLDLu cells of Example 1. Five passages were required for the PV-12 rabies strain and nine passages for the HEP Flury rabies strain in order to prepare seed virus. Three or four days after the cells were infected in suspension, when fluorescent antibody tests showed 10-50% fluorescing cells, the infected cells were detached from the glass wall of the culture vessel with trypsin-EDTA solution and resuspended in growth medium. Cells from each culture vessel used in the first cycle of growth were added to each of two fresh culture vessels for the second cycle of growth. Three to four days following the 1:2 cell split, fluorescent antibody tests of the infected cells demonstrated 100% rabies antigen positive cells. The infected fluids were harvested, pooled and stored at −70° C. in aliquots. The titers of these virus harvests ranged from $10^{5.5}$ to $10^{7.5}$ mouse $LD_{50's/ml.}$.

Example 5

By the procedure described in Example 4, using the PV-12 rabies strain in the CLDLu cells of Example 2, adaptation of the virus was accomplished by the sixth passage. Titers of the virus harvest were comparable to those indicated in Example 4.

Cultivation of Paramyxovirus in the CLDLu Cell Strain

Example 6

Parainfluenza virus type 3 was prepared from virus infected ATCC PK-15 cells, this material representing 3-4 tissue culture transfers of the virus. Four to six days after inoculation of the CLDLu cell cultures of Example 1, the cells showed marked degeneration at which time they were harvested. Cells and fluids were pooled and stored at −70° C. in aliquots. The titers of such virus harvests ranged from $10^{6.0}$ to $10^{7.0}$ $TCID_{50's/ml.}$.

Example 7

Canine distemper virus (Cabasso strain) was prepared from virus infected chick embryo suspensions, this material representing 40-45 subculture transfers of the virus. Three to four days after inoculation of the CLDLu cell suspension of Example 1, the cells showed some degeneration at which time they were harvested. Cells and fluids were pooled and stored at −70° C. in aliquots. The titers of these virus harvests ranged from $10^{3.0}$ to $10^{4.0}$ $TCID_{50's/ml.}$.

Cultivation of Herpesvirus in the CLDLu Cell Strain

Example 8

Infectious bovine rhinotracheitis virus was prepared from virus infected primary bovine kidney cells, this material representing 3-4 tissue culture transfers of the virus. Four to six days after inoculation of the CLDLu cultures of Example 1, about 75% of the cells were affected, at which time they were harvested. Cells and fluids were pooled and stored at −70° C. in aliquots. Titration of virus harvests typically gave a range from $10^{5.5}$ to $10^{6.0}$ $TCID_{50's/ml.}$.

Cultivation of Orbivirus in the CLDLu Cell Strain

Example 9

Bluetongue virus was prepared from virus infected chick embryo suspension, this material representing 45-50 subculture transfers of the virus. Four to seven days after inoculation of the CLDLu cultures of Example 1, about 75% of the cells were affected, at which time they were harvested. Cells and fluids were pooled and stored at −70° C. in aliquots. Titration of virus harvests typically gave a range from $10^{5.0}$ to $10^{6.5}$ $TCID_{50's/ml.}$.

I claim:

1. A process for the preparation of a vaccine which comprises:

(a) maintaining a culture of diploid fibroblast-like cells of a finite cell strain derived from fetal canine lung tissue in a nutrient culture medium, said cells being free of reverse transcriptase and C-type particles, being free of adventitious viruses, being non-oncogenic, and remaining diploid throughout their passage range;

(b) inoculating said medium with a virus selected from the group consisting of rabies virus, infectious bovine rhinotracheitis virus, canine distemper virus, type 3 parainfluenza virus and bluetongue virus;

(c) cultivating said virus in said medium; and, (d) recovering a harvest of said virus therefrom.

2. The process of claim 1 further including the step of rendering the virus non-infective in said harvest.

3. The process of claim 2 wherein said rabies virus includes the PV-12 strain of rabies virus.

4. A vaccine suitable for use in an animal to stimulate the production of antibodies when obtained by the process of claim 1.

5. A rabies vaccine when obtained by the process of claim 2.

6. A rabies vaccine when obtained by the process of claim 1 wherein the virus used for inoculation of the medium in step (b) is an attenuated rabies virus.

7. A process for the preparation of a rabies vaccine which comprises:

(a) maintaining a culture of diploid fibroblast-like cells of a finite cell strain in a nutrient culture medium, said cells being derived from fetal canine lung tissue and further characterized as being free of reverse transcriptase and C-type particles, free of adventitious viruses, being non-oncogenic, and remaining diploid throughout their passage range;

(b) inoculating a first portion of said cell culture with a rabies virus;

(c) serially passaging said virus for a number of passages sufficient to effect adaptation of said virus to said cells;

(d) inoculating a second portion of said cell culture with said adapted rabies virus;

(e) cultivating said adapted rabies virus; and, (f) harvesting the cultivation of said adapted rabies virus.

8. The process of claim 7 wherein said rabies virus used in step (b) is selected from the group consisting of HEP Flury and PV-12 strains of rabies virus.

9. A rabies vaccine when obtained by the process of claim 7.

10. A rabies vaccine when obtained by the process of claim 8.

* * * * *